United States Patent [19]

Sugiyama et al.

[11] Patent Number: 4,894,344
[45] Date of Patent: Jan. 16, 1990

[54] METHOD FOR MANUFACTURING 2-AMINO-2-DEOXY-D-MANNITOL

[75] Inventors: Makoto Sugiyama, Kyoto; Yoji Ezure, Otsu; Nobutoshi Ojima, Moriyama; Kiyotaka Konno; Takashi Seto, both of Kyoto; Teruya Nakamura, Kusatsu; Manabu Itoh, Otsu, all of Japan

[73] Assignee: Nippon Shinyaku Co., Ltd., Japan

[21] Appl. No.: 276,785

[22] Filed: Nov. 28, 1988

[30] Foreign Application Priority Data

Nov. 28, 1987 [JP] Japan ................................ 62/300600

[51] Int. Cl.$^4$ .................... C12R 1/56; C12R 1/465; G09B 11/08; G09B 27/08
[52] U.S. Cl. .................... 435/899; 435/886; 435/132; 435/158
[58] Field of Search ................ 435/899, 886, 158, 132

[56] References Cited

U.S. PATENT DOCUMENTS

| 3,427,224 | 2/1969 | Smiley et al. | 435/158 |
| 3,736,229 | 5/1973 | Zeeuw et al. | 435/158 |
| 4,198,481 | 4/1980 | Matsumura et al. | 435/899 |

OTHER PUBLICATIONS

*Chemical Abstracts*, Oct. 24, 1988, 109(17), p. 393, #145928n.

Primary Examiner—Ronald W. Griffin
Assistant Examiner—Pamela S. Webber
Attorney, Agent, or Firm—Jacobs & Jacobs

[57] ABSTRACT 2-amino-2-deoxy-D-mannitol is produced from a microorganism strain of the genus Streptomyces or a mutant strain thereof in improved yields and purity.

9 Claims, No Drawings

METHOD FOR MANUFACTURING 2-AMINO-2-DEOXY-D-MANNITOL

The present invention is concerned with a method for producing 2-amino-2-deoxy-D-mannitol a known substance. This compound is useful as a cosmetic, for enhancing the yield of moranoline inhibiting the blood sugar increase after meals and thus is useful in treating diabetes mellitus, when moranoline is produced from microorganisms of the genus Streptomyces (see Japanese Examined Publication No. 009919/1981).

2-amino-2-deoxy-D-mannitol has been hitherto prepared by reducing N-acetylamino-2-deoxy-D-mannose with sodium borohydride to convert it into N-acetylamino-2-deoxy-D-mannitol and then hydrolyzing N-acetylamino-2-deoxy-D-mannitol with an alkali or an acid.

The present invention comprises culturing a microorganism of the genus Streptomyces or a mutant strain thereof capable of producing 2-amino-2-deoxy-D-mannitol in a suitable culture medium, isolating the 2-amino-2-deoxy-D-mannitol from the culture medium and recovering the isolated 2-amino-2-deoxy-D-mannitol.

According to the prior art, N-acetylamino-2-deoxy-D-mannose is used as a starting material which is expensive, and difficult to obtain, and the steps for synthesis and isolation are complicated.

As a result of investigations of methods for manufacturing 2-amino-2-deoxy-D-mannitol by fermentation over a wide range, we have found that a microorganism belonging to the genus Streptomyces can produce 2-amino-2-deoxy-D-mannitol in a free form in large quantities.

A representative example of a microorganism useful in the process of the present invention is *Streptomyces lavendulae* SEN-158 which has been isolated by the present inventors from a soil sample from the city of Sapporo, Japan.

SEN-158 strain has been deposited in the Fermentation Research Institute of the Agency of Industrial Science & Technology of Japan under Accession Number of FERM P-4301. Its bacteriological properties are described in Japanese Laid Open Application No. 084094/1979. In addition, this strain has been deposited in the American Type Culture Collection (ATCC) in Rockville, Maryland under Accession Number ATC 31434.

According to the present invention, any strain other than SEN-158 is usable as long as it belongs to the genus Streptomyces and is capable of producing 2-amino-2-deoxy-D-mannitol. In addition, mutant strains obtained by applying to strains conventional treatments, such as a radiation with ultraviolet rays or $^{60}CO$ and the like, treatment with nitrogen mustard, azaserine, nitric acid, nitrosoguanidine or 2-aminopurine, transduction, transformation, cell fusion and the like, as well as naturally occurring variants or mutants, are also useful according to the present invention.

According to the present invention, the 2-amino-2-deoxy-D-mannitol producing strain is cultured in a conventional manner under the conditions used for culturing Actinomycetes. The medium used can be liquid or solid but shake culture or submerged culture in a liquid medium is generally used. The medium can be any one that is suitable for growth of Actinomycetes and capable of producing 2-amino-2-deoxy-D-mannitol.

As suitable carbon sources for the medium, one can use glucose, galactose, mannitol, sucrose, maltose, glycerine, dextrin, starch, or the like. As suitable sources of nitrogen for the medium, one can use soybean powders, peptone, yeast extract, meat extract, corn steep liquor, ammonium chloride, ammonium sulfate, ammonium nitrate, urea, and the like.

In addition, the culture medium can be supplemented by the addition of sodium chloride, potassium chloride, calcium carbonate, various phosphates or the like in a suitable amount. In addition, iron, magnesium and the like may also be added as supplements.

If necessary or desirable, organic or inorganic compounds, vitamins, and the like can be added to accelerate the growth of the microorganisms used for the production of 2-amino-2-deoxy-D-mannitol.

In case foaming occurs to an extent greater than desirable during fermentation, a defoaming agent may be used as needed.

Conditions for incubation such as the pH of the medium, the incubation temperature and the like can be varied within a range that optimizes the production of 2-amino-2-deoxy-D-mannitol by those skilled in the art. For example, in shake culture or submerged culture, it is desired to culture at a pH of from 6 to 9 at an incubation temperature from approximately 20° C. to about 35° C., preferably 25° C. to 30° C.

The period of incubation varies depending upon the scale of the culture and other conditions, but it is generally sufficient to conduct the incubation for a period of 2 to 20 days.

After the incubation, the cells are separated and the product is isolated from the obtained culture broth and purified. Isolation and purification of the 2-amino-2-deoxy-D-mannitol of the present invention from the culture broth can be accomplished by a conventional technique used for isolating and purifying microorganism metabolites from culture broths. For example, adsorption and desorption with various adsorbents such as silica gel, alumina, activated charcoal, ion exchange resins and the like, chromatography, partition chromatography and the like can be used singularly or in combination.

The following non-limitative examples more particularly illustrate the present invention.

EXAMPLE 1

In a 500 ml Erlenmeyer flask, 100 ml of medium containing (8% of soluble starch, 1% of soybean powders, 1% of yeast extract, 0.05% of potassium chloride, 0.05% of magnesium sulfate, 0.5% of sodium chloride and 0.2% of sodium nitrate, pH 7.2) was charged and sterilized. Several platinum loops of SEN-158 strain were inoculated to the medium from the slant followed by shake culture at 27° C. for 3 days to give a preculture solution. This preculture solution, 300 ml, was inoculated on 15 liters of culture solution (components are the same as in the preculture solution) charged in a 30 liter volume jar fermenter followed by culture at 27° C. for 11 days.

As a defoaming agent, NISSAN DISFOAM CB-442 was used; an aeration rate and an agitation speed were 20 liters/min. and 300 rpm, respectively.

After 12.9 liters of the obtained culture broth was centrifuged at 9000 rpm for 20 minutes, the obtained supernatant was passed through a column packed with strongly acidic ion exchange resin Dowex 50W×2

(H+) (1 liter). After thoroughly washing with water, elution was performed with 1 N ammonia water.

The eluate was concentrated under reduced pressure. The concentrate was passed through strongly basic ion exchange resin Diaion SA-11A (OH) (500 ml) followed by eluting water. The eluate was combined with the washing liquid. The mixture was concentrated under reduced pressure. The concentrate was allowed to stand at 5° C. for several days. The formed crystals were collected and recrystallized from 20% hydrated ethanol to give 1 g of 2-amino-2-deoxy-D-mannitol. Physical properties of this product are as follows.

Melting point: 161°–163° C.
Elemental analysis ($C_6H_{15}NO_5$)
Calcd. (%) C: 39.77 H: 8.34 N: 7.73
Found (%) C: 39.62 H: 8.17 N: 7.81
Specific rotary power $[\alpha]_D^{24} + 4.0°$ (C=1%, water)
$^{13}$C-NMR ppm; ($D_2O$, internal standard; methanol 49.8 ppm)
53.84 64.05 64.31 70.73 71.29 71.85
$^1$H-NMR ppm; ($D_2O$, internal standard; DSS)
2.98–3.12 (1H, m), 3.56–3.90 (7H, m)

The structure of this product was confirmed by the fact that the properties were fully identical with those of a compound synthesized by reducing N-acetylamino-2-deoxy-D-mannitol with sodium borohydride and then hydrolyzing it with hydrochloric acid.

Test Example

Effect of 2-amino-2-deoxy-D-mannitol on moranoline production

Variant GC-148 of newly isolated moranoline-producing strain MB-733 belonging to the genus Streptomyces was inoculated on a medium shown below. After shake culture at 27° C. for 7 days, 10 ml of the culture broth was centrifuged. The supernatant was passed through a column packed with strongly acidic ion exchange resin Dowex 50W×2 (H+) (1 liter). After thoroughly washing with water, elution was performed with 0.5 N ammonia water. After the eluate was concentrated to dryness under reduced pressure, the residue was dissolved in 1 ml of water. The solution was subjected to high performance liquid chromatography to quantitatively determine moranoline.

Conditions for high performance liquid chromatography were as follows: column, Nucleosil 5NH$_2$; developing solvent, acetonitrile-water=7:3; detection, differential refractometer.

Medium A: 2% of soluble starch, 1% of soybean powders, 1% of yeast extract, 0.05% of potassium chloride, 0.05% of hydrated magnesium sulfate, 0.5% of sodium chloride, 0.2% of sodium nitrate and 0.35% of calcium carbonate; pH 7.0

Medium B: medium obtained by supplementing 1% of 2-amino-2-deoxy-D-mannitol to Medium A The results are shown in the table below.

|  | pH | Moranoline (μg/ml) |
| --- | --- | --- |
| Medium A | 8.6 | 981 |
| Medium B | 7.6 | 4428 |

The enhancing effect of 2-amino-2-deoxy-D-mannitol on the production of moranoline is clear from the above results.

What is claimed is:

1. A process for the production of 2-amino-2-deoxy-D-mannitol which comprises culturing a 2-amino-2-deoxy-D-mannitol producing strain of the genus Streptomyces in a medium suitable for culturing Actinomycetes, isolating the 2-amino-2-deoxy-D-mannitol from the culture medium and recovering the isolated 2-amino-2-deoxy-D-mannitol.

2. A process according to claim 1 wherein the culture medium is liquid.

3. A process according to claim 1 wherein the culture medium is solid.

4. A process according to claim 2 wherein the culture medium is a shake culture or submerged culture in a liquid medium.

5. A process according to claim 1 wherein the cells are separated and the 2-amino-2-deoxy-D-mannitol is isolated from the culture broth.

6. A process according to claim 5 wherein the 2-amino-2-deoxy-D-mannitol is purified and isolated from the culture broth.

7. A process according to claim 1 wherein the strain is Streptomyces lavendulae SEN-158.

8. A process for the production of 2-amino-2-deoxy-D-mannitol which comprises culturing a 2-amino-2-deoxy-D-mannitol producing strain of the genus Streptomyces in a suitable culture medium containing sufficient sources of carbon and nitrogen to culture said microorganism, separating the cells formed from the culture medium, isolating the 2-amino-2-deoxy-D-mannitol from the culture broth, purifying the isolated 2-amino-2-deoxy-D-mannitol and recovering the isolated, purified 2-amino-2-deoxy-D-mannitol produced.

9. A process according to claim 1 which further comprises adding to the culture medium a growth accelerating amount of a growth accelerator.

* * * * *